United States Patent [19]

Mossholder

[11] Patent Number: Plant 7,530

[45] Date of Patent: May 21, 1991

[54] AZALEA HYBRID 'BILLIE DEE'

[75] Inventor: Rose M. Mossholder, Fallbrook, Calif.

[73] Assignee: Hines Nurseries Inc., Irvine, Calif.

[21] Appl. No.: 352,306

[22] Filed: May 16, 1989

[51] Int. Cl.[5] ..... A01H 5/00

[52] U.S. Cl. ..... Plt./57

[58] Field of Search ..... Plt./55, 57

*Primary Examiner*—Howard J. Locker

*Attorney, Agent, or Firm*—Klarquist, Sparkman, Campbell, Leigh & Whinston

[57] ABSTRACT

The new plant is a hybrid evergreen azalea having a compact, dense branching and symmetrical form and a prolific blooming habit. Flowers appear in clusters of five to ten. The blossoms are of single form with a diameter of about 6.4 to 7.6 cm and have pale lilac centers bordered with rose-purple lobes. The plant blooms mid-February through mid-April in southern California.

3 Drawing Sheets

BACKGROUND OF THE INVENTION

The present invention relates to a new and distinct variety of evergreen azalea of the genus Rhododendron and a member of the Ericaceae family. This new variety of azalea plant is the result of a breeding program. The principal objectives of this breeding program were to produce new varieties of evergreen azaleas which are floriferous, compact, vigorous, and easy to propagate using vegetative cuttings.

The specific parentage of the new variety is unknown because no records were kept of the crosses that resulted in the new plant. The breeding program incorporated the use of 47 varieties of evergreen azaleas from seven hybrid groups that were grown at the Mossholder Nurseries in La Habra, Calif.

Hybrid Groups Used in the Breeding Program

| | # of Cultivars |
|---|---|
| Belgian Indian Hybrids | 25 |
| Coolidge Hybrids | 3 |
| Mossholder-Bristow Hybrids | 11 |
| Pericat Hybrids | 2 |
| Rutherford Hybrids | 2 |
| Southern Indian Hybrids | 1 |
| Kurume Hybrids | 3 |

'Billie Dee' most closely resembles the Satsuki group of hybrid azaleas.

This new hybrid has the following combination of characteristics which distinguish it from other varieties.

1. Flower color pattern, form and season of bloom. The blooms have pale lilac centers bordered with rose purple lobes. The plant has single 6.4 to 7.6 cm blooms which occur mid season (February–April) in southern California.

2. Plant form and vigor. The plant is naturally compact and very vigorous.

3. Ease of vegetative propagation. The new hybrid has been reproduced thousands of times by cuttings at Hines Nurseries in Irvine, Calif. Each of the progeny exhibit characteristics identical to the original mother plant, establishing the hybrid as reproducible and true to type.

DESCRIPTION OF THE PHOTOGRAPHS

DETAILED PLANT DESCRIPTION

Figure 1:
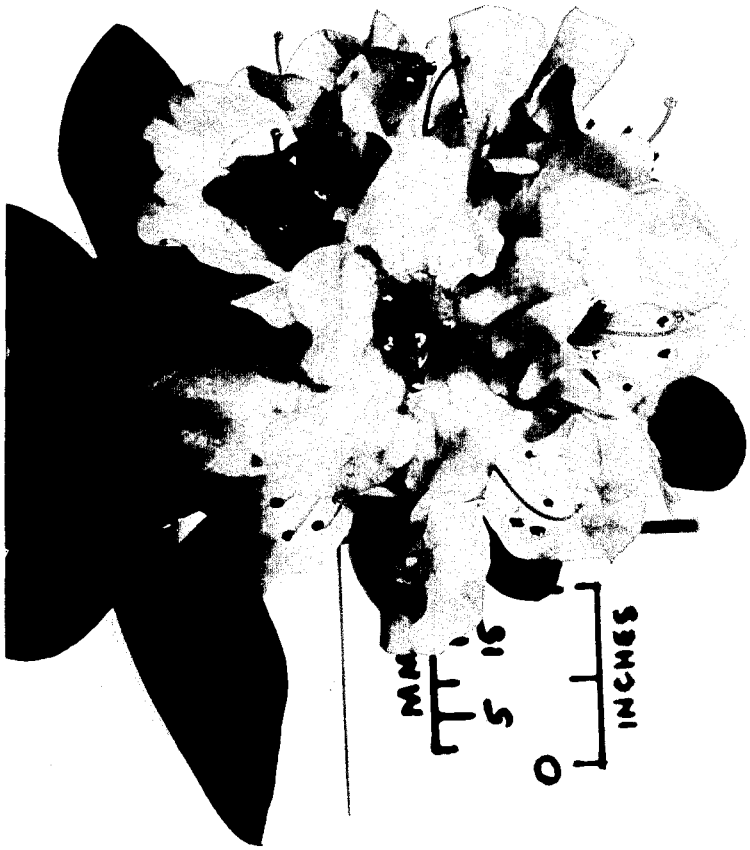
FIG. 1 is a closeup of a flower cluster of azalea 'Billie Dee' demonstrating the color pattern and size.
Figure 2:
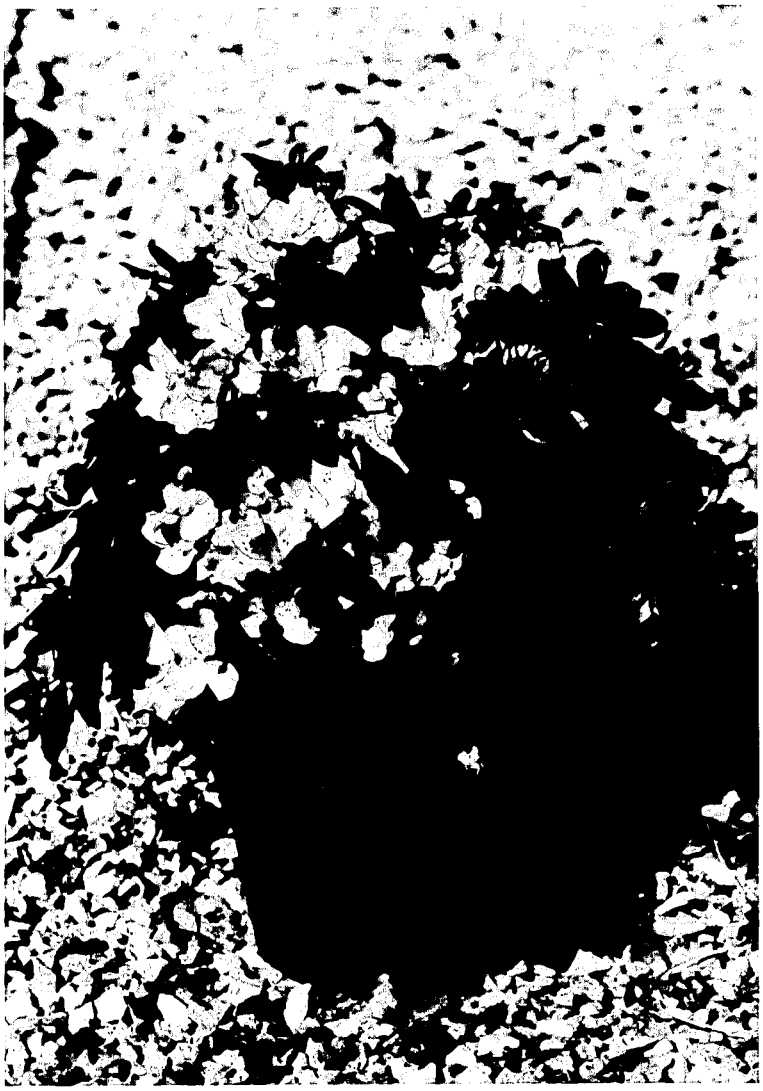
FIG. 2 is a photograph showing the overall appearance showing the naturally compact growth habit and prolific blooming habit.
Figure 3:
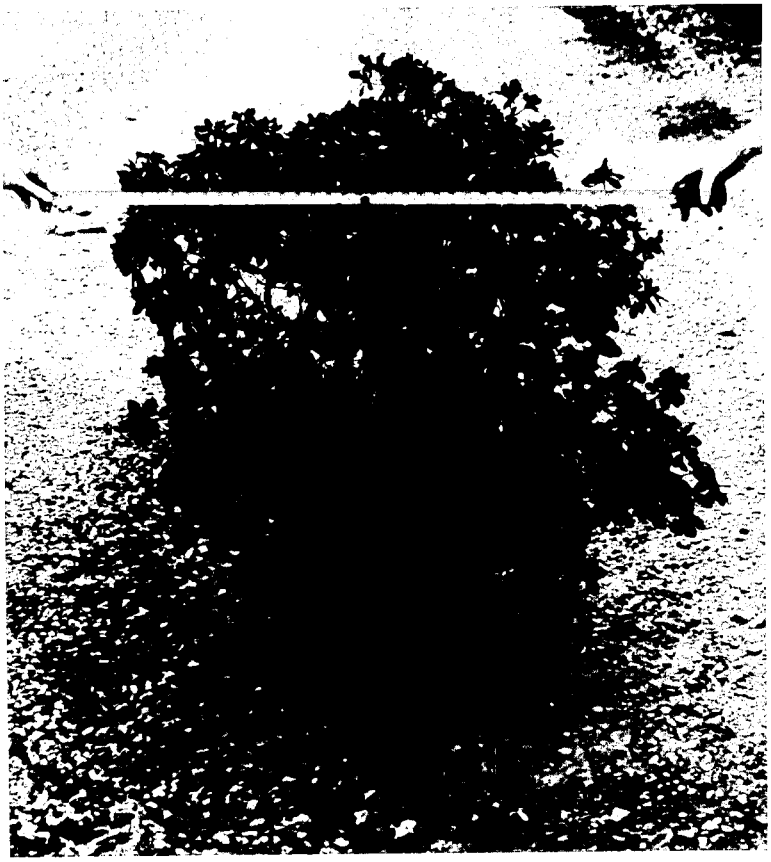
FIG. 3 is a photograph of a nearly mature 9 year old plant that has just passed the blooming stage.

The following is a description of the new hybrid azalea plant. Color determinations and comparisons are all based on the Royal Horticultural Society Colour Chart.

Origin: Hybrid seedling.
Parentage: Unknown.
Classification: Hybrid.

Form: Globose and compact. Dense, twiggy branching. Symmetrical. Branch positions are whorled.

Growth: Active, strong rapid growth on the plant's own rootstock (vigorous). Estimated annual terminal growth averages about 15 cm.

Size: Height of a 9 year old plant in a #15 container reached 81.5 cm (32 inches) with a width of 109 cm (43 inches). The estimated height for a mature plant (older than 10 years) is 90 cm with an approximate width of 120 cm.

Blooming habit: Prolific.

Blooming period: Blooms appear in mid-February and continue through mid-April in Irvine, Calif.

Disease resistance: Normal, as determined by comparison with other azalea varieties grown under the same cultural conditions at Irvine, Calif.

Hardiness: Minimum temperature for 'Billie Dee' is normally about −7° to −1° C. (20° to 30° F.). Minor frost damage occurred to newly formed foliage and flower buds on Feb. 14, 1990 in Irvine, Calif. when the temperature dropped to −3.3° C. (26° F.). The plant has not been tested for maximum cold hardiness.

FOLIAGE

Arrangement: Alternate.

Type: Evergreen.

Shape: Oblanceolate to obovate, broadly acute to obtuse, cuneate, flat.

Size:

*Average length of mature foliage (from petiole to leaf apex).*—5.4 cm.

*Average width of mature foliage.*—2.7 cm.

Color:

*Upper surface.*—Fan 3, Yellow-Green Group No. 139A.

*Lower surface.*—Fan 3, Yellow-Green Group No. 146B.

Margins: Entire, ciliate.

Texture: Coarse and glossy.

*Immature leaves.*—Sericeous, indumentum color Orange-White Group No. 159B.

*Mature leaves.*—Strigose, indumentum color Orange-White Group No. 159C.

Petiole: Average length 0.5 cm. Sericeous, coppery brown color Yellow-Green Group No. 144B, C.

Buds: Elliptic, color Yellow-Green Group No. 144A. Buds are covered with copper brown sericeous hairs, color Grey-Yellow Group No. 161B, C.

Stems:

*Immature growth.*—Color Yellow-Green Group No. 146C with sericeous to strigose hairs ranging in color from Grey-Orange Group No. 164D to Orange-White Group No. 159D.

*Mature growth.*—Color Grey-Orange Group No. 164A with whitish to copper brown strigose hairs ranging in color from Orange-White Group No. 159A to Grey-Orange Group No. 165A.

INFLORESCENSE

Blooming period: Mid-February through mid-April at Irvine, Calif.

Inflorescense: Complete and perfect.

Borne: In clusters of five to ten.

Petalage: Five lobes fused at base. Rounded shape, undulate margins, soft and satiny texture.

Form: Single, openly funnel shaped.

Size: Medium, 6.4 to 7.6 cm in diameter and 3.5 to 4.5 cm in length.

Pedicel: Length 0.9 cm; color Yellow-Green Group No. 145C with occasional pink blushing and whitish sericeous hairs color Orange-White Group No. 159A.

Color:

*Petal surface.*—Corolla tube color is Red-Purple Group No. 69B; from petal edge for about 1.3 to 2.0 cm are Fan 2, Red-Purple Group No. 72C. Approximately 37% to 44% of the corolla area is the darker color. The dots on the standard petal are color Red-Purple Group No. 67B.

Persistence: Petals hang and dry. Color turns to various shades of red-purple to brown and discolors with age.

Calyx: Persistent, ovate, valvate with length averaging 0.5 cm. Color Yellow-Green Group 145A with sericeous whitish hairs.

Flower buds: Buds were observed and measured at an approximate age of two weeks when still tight. They were elliptic and medium acute in shape with a length of 3 cm and width of 0.5 cm. The color is not significantly different from the color of the open flowers except that the petal margins appear to be a slightly darker shade of red-purple.

REPRODUCTIVE ORGANS

Stamens: Stamens have Grey-Orange Group No. 165B color anthers and Orange-White Group No. 159A filaments, varying slightly dependent on maturity. White pollen present but not tested for viability.

Pistils: Single pistil with average length of 3.8 cm, equal to or longer than petal length, almost twice as long as stamens. Immature style is Red Group No. 54A with Red Group No. 52A stigma. Mature style is Red Group No. 53C, D with Red Group No. 53A stigma.

Ovary: Five locules within a hypogynous ovary enclosed by a sericeous ovary wall. Seed observed but not tested for viability.

DESCRIPTIONS OF MOST SIMILAR KNOWN AZALEA CULTIVARS

Azalea 'Billie Dee' has lilac centered blossoms which are bordered with rose purple margins. The plant blooms in mid-season in southern California and has single blossoms 6.4 to 7.6 cm in diameter. The following five cultivars are the most similar that the applicant is aware of in the nursery trade. The first three of these are possible ancestors.

'Desert Rose': Single, strong pink, lighter throat, red flecks, frilled, 9 to 10 cm diameter blossoms. Blooms early to mid season.

'Easter Bonnet': Single, purplish pink, white throat and greenish flecks, 7.6 cm in diameter. Blooms in late season.

'Professor Wolters': Single, salmon rose edged white. Large 10 cm diameter blossoms. Blooms late season.

These Satsuki Hybrids are also somewhat similar.

'Geisha Girl': Single, white center bordered rose red, round petals, medium sized, late season bloomer.

'Shinyo-No-Tsuki': Single, purplish red with white center, late season bloomer.

I claim:

1. A new variety of hybrid evergreen azalea characterized by a compact, dense branching and symmetrical form and a prolific blooming habit, with flowers that appear in clusters of five to ten, blooms being of single form with a diameter of about 6.4 to 7.6 cm and having pale lilac centers bordered with rose-purple lobes.

* * * * *